United States Patent [19]

Oi et al.

[11] 4,355,038
[45] Oct. 19, 1982

[54] α-SUBSTITUTED UREIDO-BENZYLPENICILLANIC ACIDS

[75] Inventors: Nobuhiro Oi, Houya; Bunya Aoki, Tanashi; Teizo Shinozaki, Hasuda; Kanji Moro, Kuki; Toshio Kuroki; Isao Matsunaga, both of Tokyo; Takao Noto, Machida; Toshiyuki Nebashi, Kawagoe; Yusuke Harada; Hisao Endo, both of Tokyo; Takao Kimura, Chiba; Kana Kojima, Mitaka; Masahiko Matsumoto, Kawasaki; Hiroshi Okazaki, Sayama; Haruki Ogawa, Chofu; Minoru Shindo, Tokyo, all of Japan

[73] Assignee: Chugai Seiyaku Kabushiki Kaisha, Tokyo, Japan

[21] Appl. No.: 288,402

[22] Filed: Jul. 30, 1981

[30] Foreign Application Priority Data

Aug. 5, 1980 [JP] Japan .................. 55-106775

[51] Int. Cl.³ .............. A61K 31/43; C07D 499/68
[52] U.S. Cl. ................... 424/271; 260/239.1
[58] Field of Search ............... 260/239.1; 424/271

[56] References Cited

U.S. PATENT DOCUMENTS

| 3,931,405 | 1/1976 | Ekstrom et al. ........ 260/239.1 |
| 3,933,795 | 1/1976 | Disselnkotter et al. . |
| 3,936,442 | 2/1976 | König et al. . |
| 3,939,149 | 2/1976 | König et al. . |
| 3,959,258 | 5/1976 | König et al. . |
| 3,974,140 | 8/1976 | König et al. . |
| 3,978,223 | 8/1976 | König et al. . |
| 3,980,792 | 9/1976 | König et al. . |
| 4,016,282 | 4/1977 | König et al. . |
| 4,229,348 | 10/1980 | Oi et al. . |
| 4,240,960 | 12/1980 | Walker et al. . |

FOREIGN PATENT DOCUMENTS

| 877295 | 12/1979 | Belgium . |
| 1904851 | 5/1970 | Fed. Rep. of Germany . |
| 2311328 | 10/1973 | Fed. Rep. of Germany . |
| 53-35321 | 1/1978 | Japan . |
| 1250611 | 10/1971 | United Kingdom . |
| 1260882 | 1/1972 | United Kingdom . |
| 1301961 | 1/1973 | United Kingdom . |
| 1426199 | 2/1976 | United Kingdom . |
| 1562802 | 3/1980 | United Kingdom . |

Primary Examiner—Natalie Trousof
Assistant Examiner—Vera C. Clarke
Attorney, Agent, or Firm—Browdy and Neimark

[57] ABSTRACT

α-Substituted ureido-benzylpenicillanic acids of the formula

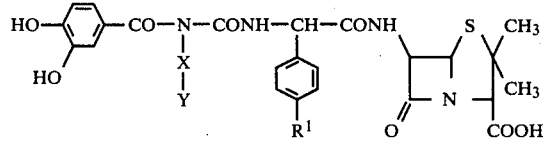

(wherein $R^1$, X and Y are as defined in the description) and pharmaceutically acceptable salts thereof, and a bactericidal composition comprising the above penicillanic acid or the salt and a pharmaceutically acceptable carrier are disclosed. The acids and salts thereof have high antibacterial activities against Gram-positive and Gram-negative bacteria, particularly those of the genus Pseudomonas.

4 Claims, No Drawings

α-SUBSTITUTED UREIDO-BENZYLPENICILLANIC ACIDS

This invention relates to a compound of the formula (I):

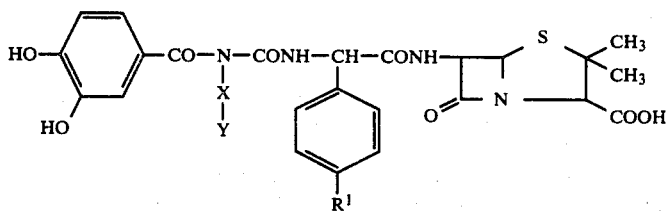

[wherein $R^1$ is a hydrogen atom or a hydroxyl group; X is a lower alkyl group of $C_{2-3}$; and Y is bonded to a terminal carbon atom of the substituent of X and means the group $—OR^2$ (wherein $R^2$ is a hydrogen atom, a lower alkyl group of $C_{1-2}$, a lower alkanoyl group of $C_{2-3}$ or a lower alkyl group of $C_{2-3}$ substituted with a hydroxyl group)] or a pharmaceutically acceptable salt thereof, and a bactericidal composition comprising the above compound or a pharmaceutically acceptable salt thereof.

British Pat. Nos. 1,250,611, 1,301,961, 1,426,199, as well as U.S. Pat. Nos. 3,931,405, 3,933,795, 3,936,442, 3,939,149, 3,959,258, 3,974,140, 3,978,223, 3,980,792, 4,016,282, West German Patent Offenligungsschrift No. 2,311,328, Belgium Pat. No. 877,295 and Japanese Patent Public Disclosure No. 3532/78 disclose a variety of α-benzoylureido-α-benzylpenicillins, but none of these prior art references make mention of compounds wherein the benzoyl group is substituted by a hydroxyl group.

British Pat. No. 1,260,882 discloses α-benzoylureido-α-benzylpenicillins having 4-chloro-3-hydroxybenzoyl group, 3-chloro-4-hydroxybenzoyl group, or m-hydroxybenzoyl group as the benzoyl group. However, it makes no mention of a benzoyl group having two hydroxyl groups.

West German Patent Offenlegungsschrift No. 1,904,851 discloses a variety of α-benzoylureido-α-benzylpenicillins. Although it discloses a compound wherein the benzoyl group is substituted by a hydroxyl group, that is, D-α-(N-p-hydroxybenzoylureido) benzylpenicillin, no mention is made of a compound wherein the benzoyl group is substituted by two hydroxyl groups.

The inventors of this application filed patent applications in many countries with respect to an invention directed to a group of penicillanic acid derivatives having 3- and 4-hydroxy groups on the phenyl nucleus of the α-benzoylureido moiety, and the invention has been published in some countries, for example, as U.S. Pat. No. 4,229,348 and West German Patent Offenlegungsschrift No. 2,921,348. However, the substituent of these derivatives corresponding to the group of —X—Y of the compound of this invention is a hydrogen atom or a lower alkyl group and, therefore, the derivatives clearly differ in chemical structure from those of this invention.

The α-substituted ureido-benzylpenicillins of the formula (I) are undocumented novel compounds. They have high antibacterial activity against Gram-positive and Gram-negative bacteria, perticularly those of the genus Pseudomonas, and they have higher in vivo activity than any of the known compounds. Therefore, the compounds of the formula (I) and pharmaceutically acceptable salts thereof are useful as an antibacterial agent.

One object of this invention is to provide an effective antibacterial compound of the formula (I) and a pharmaceutically acceptable salt thereof.

Since the α-substituted ureidobenzylpenicillins of this invention have a carboxyl group at 3-position, they are capable of forming salts with various basic materials on the carboxyl group, and among the so formed salts, those with pharmaceutically acceptable basic materials are important. Examples of such salts include inorganic base salts, for example, salts of alkali metals (e.g. sodium and potassium) and salts of alkaline earth metals (e.g. calcium). These salts may be produced by the conventional technique namely, by treating the carboxyl group with an equivalent molar amount of the basic materials described above.

Because of the presence of an asymmetric carbon atom in the 6-acetamide group, the compounds of this invention include optical isomers, i.e., DL-, D- and L-isomers, and in some cases, even a diastereomer and these isomers are included in the definition of the α-substituted urediobenzylpenicillins of this invention.

The compounds of the formula (I), or the α-substituted ureidobenzylpenicillins, can be produced by various methods. According to one method, α-substituted ureidophenylacetic acid of the formula (II):

$$R^3 \underset{R^3}{\underbrace{\phantom{XXX}}} \!\!\!-CON-CONH-CH-COOH \quad\text{(II)}$$
$$\overset{|}{X} \quad \overset{|}{Y^1} \quad \underset{R^{11}}{\underbrace{\phantom{XXX}}}$$

(wherein $R^{11}$ is a hydrogen atom, hydroxyl group or a protected hydroxyl group, $R^3$ is a hydroxyl group or a protected hydroxyl group, $Y^1$ is either the same as Y in the formula (I) or Y containing a protected hydroxyl group, and X is the same as X in the formula (I)) or a reactive derivative thereof is reacted with 6-aminopenicillanic acid of the formula (III):

$$H_2N\!-\!\!\!\underset{O}{\overset{\phantom{X}}{\underset{\|}{\diagup}}}\!\!\!\underset{N}{\overset{S}{\diagdown}}\!\!\!\underset{COOR^4}{\overset{CH^3}{\diagdown CH^3}} \quad\text{(III)}$$

(wherein $R^4$ is a hydrogen atom or a protecting group) or a reactive derivative thereof, and the protecting group, if any, in $R_{11}$, $R_3$, $R_4$ or $Y_1$ of the formula (II) may be any group that can be easily removed.

The protecting group of the hydroxyl group contained in $R^{11}$, $R^3$ or $Y^1$ of the formula (II) may be any group that can be easily removed under mild conditions. Examples are an acyl group such as a formyl group, acetyl group, propionyl group, butyryl group, or chloroacetyl group; an aralkyl group such as a benzyl group, benzhydryl group or trityl group; a substituted aralkyl group having a substituent such as methoxy group or nitro group on the aryl nucleus of these aralkyl groups; a monovalent silyl group such as a trimethylsilyl group, triethylsilyl group, dimethylmethoxysilyl group, diethylmethyoxysilyl group, trimethoxysilyl group, or triethoxysilyl group in case of protecting adjacent two hydroxyl groups; a divalent silyl group such as a dimethylsilyl group; and a group conventionally used to protect the hydroxyl group such as a t-butyl group, methoxymethyl group, phenacyl group or a tetrahydropyranyl group.

The reactive derivative of the α-substituted ureidophenylacetic acid of the formula (II) is such that the carboxyl group to be involved in the reaction is activated, and examples are an acid anhydride, active ester, active amide and acid halide.

More specifically, the reactive derivative is illustrated by a mixed anhydride with an aliphatic carboxylic acid such as pivalic acid, trichloro-acetic acid or pentanoic acid; a mixed anhydride with alkyl carbonic acid; a mixed anhydride with phenylphosphoric acid; a mixed anhydride with aromatic carboxylic acid; an ester such as 1-hydroxybenzotriazolyl ester, 2,4-dinitrophenylester, N-hydroxysuccinimidyl ester, N-hydroxyphthalimidyl ester, pentachlorophenyl ester, phenylazophenyl ester, cyanomethyl ester and methoxymethyl ester; and an acid amide with imidazole, triazole or tetrazole.

When $R^4$ in the formula (III) means a protecting group, particularly, an ester-forming group, the amide-bond forming reaction may be performed efficiently by using a carbodiimide (e.g. N,N'-dicyclohexylacarbodiimide, N,N'-diethylcarbodiimide, N-cyclohexyl-N'-morpholinoethylcarbodiimide or N,N'-diisopropylcarbodiimide as a condensing agent for the substituted ureidophenylacetic acid that is not converted to a reactive derivative but which remains a carboxylic acid.

When all of the hydroxyl groups contained in $R^{11}$, $R^3$ and $Y^1$ of the formula (II) are protected, the α-substituted ureidophenylacetic acid may be subjected to the reaction in the form of a halide. The acetic acid can be converted to a halide by either treating it with a conventionally used halogenating agent such as oxalyl chloride or thionyl chloride, or by treating the same with a Vilsmeyer's reagent obtained by reaction between dimethylformamide or N-methylformanilide and thionyl chloride, phosphorous oxychloride, trichloromethyl chloroformate or phosgene.

When $R^4$ of the 6-aminopenicillanic acid of the formula (III) is a protecting group, examples of such protecting group include a salt-forming organic or inorganic base such as alkali metal, alkaline earth metal, triethylamine, N-methylpiperidine and pyridine; a halogenated lower alkyl group such as a chloromethyl group, 2,2,2-trichloroethyl group or 2,2,2-trifluoroethyl group; an aralkyl group such as a benzyl group, benzhydryl group or trityl group; a substituted aralkyl group having a substituent such as methoxy or nitro group on the aryl nucleus of these aralkyl groups; and a silyl group such as a trimethylsilyl group; triethylsilyl group, dimethylmethoxysilyl group, diethylmethoxysilyl group, trimethoxysilyl group or triphenylsilyl group.

The reactive derivative of the 6-aminopenicillanic acid means a derivative wherein the 6-amino group is activated. The 6-amino group may be activated by, for example, introducing a silyl group such as trimethylsilyl group into the 6-amino group.

The amide-bond forming reaction is preferably performed in an inert organic solvent such as acetone, tetrahydrofuran, dimethylformamide, acetonitrile, dioxane, chloroform, dichloromethane, dichloroethane or ethyl acetate. A hydrophilic inert organic solvent may be used as a mixture with water. The reaction is usually performed under cooling or at room temperature but it may be performed under heating. To be more specific, the reaction temperature is usually selected from the range of −30° to 30° C., and preferably it is selected from the range of 0° to 10° C. when the α-substituted ureidophenylacetic acid is used in the form of an active ester or active amide, and from the range of −15° to −5° C. when it is used in the form of an acid anhydride, and from the range of −20° to −10° C. when it is used in the form of an acid halide. The reaction period varies with the reaction temperature, the compound subjected to the reaction, the solvent used, etc., but it is properly selected from the range of 0.5 to 48 hours, preferably from 1 to 24 hours.

After completion of the amide-bond forming reaction, any protecting group present in the reaction product is removed. If the protecting group for the hydroxyl group in $R^{11}$, $R^3$ and $Y^1$ is an acyl group, it can be removed by treatment with an inorganic or organic base. Examples of the inorganic base include a hydroxide of alkali metal such as sodium hydroxide or potassium hydroxide; a hydroxide of alkaline earth metal such as magnesium hydroxide or calcium hydroxide; a carbonate salt of alkali metal such as sodium carbonate or potassium carbonate; a carbonate salt of alkaline earth metal such as magnesium carbonate or calcium carbonate; a bicarbonate salt of alkali metal such as sodium hydrogencarbonate or pottassium hydrogencarbonate; a phosphate salt of alkaline earth metal such as calcium phosphate; a hydrogenphosphate salt of alkali metal such as disodium hydrogenphosphate or dipotassium hydrogenphosphate; and ammonia. Examples of the organic base include an acetate salt of alkali metal; a trialkylamine such as trimethylamine or triethylamine; and an alcoholamine such as diethylaminoethanol or triethanolamine. The removal of the acyl group with these bases is performed in water or organic solvents containing an alcoholic hydroxyl group (e.g. methanol, ethanol or ethanolamine) or a mixture thereof. Preferred examples are methanolic ammonia and a triethylamine/triethanolamine/dimethylformamide mixture.

If the protecting group is an aralkyl or a substituted aralkyl group, it may be removed by catalytic reduction, for example, by catalytic reduction using palladium-carbon. If the protecting group is a t-butyl group, methoxymethyl group, phenacyl group, tetrahydropyranyl group or silyl group, it can be removed with an inorganic acid such as hydrochloric acid.

The protecting group by which $R^4$ in the formula (III) is meant can be removed by reduction with a metal and acid, say, zinc-acetic acid if the protecting group is a halogenated lower alkyl group, and by catalytic reduction with, say, palladium-carbon, or by using organic or inorganic acids such as formic acid, trifluoroacetic acid, benzenesulfonic acid, p-toluenesulfonic acid, hydrochloric acid or a cationic ion-exchange resin or a Lewis acid such as aluminum chloride if the protecting group is an aralkyl group or a substituted aralkyl group. If the protecting group is a silyl group, it can be removed by either the acids mentioned above or an alcohol such as methanol. If $R^4$ is a salt-forming base, it can be removed by treatment with an acid.

The object compound can be isolated from the reaction mixture and the isolate can be purified easily by any of the conventional techniques, for example, by extraction with an organic solvent such as dichloromethane, chloroform, tetrahydrofuran or ethyl acetate, or by various techniques of chromatography using activated carbon, silica gel, ion exchange resin, crosslinked dextran polymer or a high porous polymer of styrenedivinylbenzene or acrylic ester.

The α-substituted ureidophenylacetic acid of the formula (II) is a novel compound, and it can be produced by, for example, reacting a corresponding α-aminophenylacetic acid with a corresponding N-substituted benzoyl-N-substituted alkylcarbamic acid halide having a protected hydroxyl group, and by removing the protecting group if necessary. For the applicable protecting groups and the means to remove them, see the foregoing description of the protecting groups for $R^3$, $R^{11}$ and $Y^1$.

According to another method of producing the compounds of the formula (I), or the α-substituted ureidobenzylpenicillins, an N-benzoylcarbamic acid halide of the formula (IV):

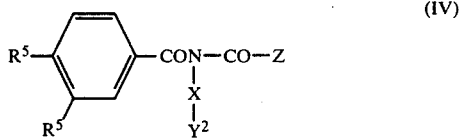

(wherein $R^5$ is a protected hydroxyl group, $Y^2$ is a protected hydroxyl group, a lower alkoxyl group of $C_{1-2}$, a lower alkanoyloxy group $C_{2-3}$ or a lower alkoxyl group of $C_{2-3}$ substituted with a protected hydroxyl group, and Z is a halogen atom is reacted with an α-aminobenzylpenicillin of the formula (V):

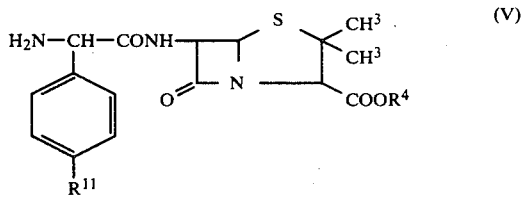

(wherein $R^{11}$ and $R^4$ have the same meaning as defined above) or a reactive derivative thereof, and any protecting group that is present in the resulting product is removed.

The protecting groups in $R^5$ and $Y^2$ in the formula (IV) have the same meanings as defined for the protecting groups in $R^3$ and $Y^1$. The reactive derivative of the α-aminobenzylpenicillins of the formula (V) is such that the α-amino group is activated by introducing in it a silyl group such as trimethyl silyl group.

The reaction is preferably performed in an inert organic solvent such as acetone, tetrahydrofuran, acetonitrile, dimethylformamide, dioxane, chloroform, dichloromethane, dichloroethane or ethyl-acetate. The reaction is usually performed under cooling or heating, preferably at a temperature between 0° and 30° C. The reaction period is usually selected from the range of 1 to 48 hours, preferably from 1 to 10 hours. The protecting group present in the reaction product is removed by the same technique as described for removal of the protecting groups from $R^{11}$, $R_3$, $R^4$ and $Y_1$. The object compound can be isolated from the reaction mixture and the isolate can be purified by the same method as described for the first method of producing the α-substituted ureidobenzylpenicillin.

The N-benzoylcarbamic acid halide of the formula (IV) is a novel compound and it can be produced by treating a corresponding benzamide or its derivative with a carbonylating agent such as phosgene, trichloromethyl chloroformate in solvent such as dichloromethane, tetrahydrofuran or ethyl acetate.

An isomer of the α-substituted ureidobenzylpenicillins of the formula (I) can be produced efficiently by the same method as described above except that an α-substituted ureidophenylacetic acid (formula (II)) and α-aminobenzylpenicillin (formula (V)) having the desired optical activity. The desired optically active substance can be obtained by using a conventional optical resolution technique.

The object compound of this invention, or the compound of the formula (I), and pharmaceutically acceptable salts thereof can be formulated into pharmaceutical preparations adapted to various administration routes in a manner similar to that used for other penicillin compounds. Therefore, one aspect of this invention is various pharmaceutical compositions adapted for human beings or animals. These compositions are provided by a conventional method using a necessary pharmaceutical carrier, diluent and/or excipient. An injection may be prepared by formulating the compound into a suspension, solution or emulsion in an oily or aqueous vehicle. A suppository can also be made of the compound by using a conventional suppository base such as coconut oil or other glycerides.

The content of the active compound varies depending on the administration route, but usually it is above 0.1%, say between 5 and 99%, and preferably between 10 and 60%. The amount of administration for human beings is usually in the range of 100 to 3000 mg per day for an adult. The daily administration in an amount of 500 to 2000 mg is preferred for an adult though the exact amount varies with the route and frequency of administration, body weight, age, and the conditions of the patient.

To demonstrate the pharmaceutical advantages of the end compounds of this invention, the minimum inhibitory concentration (MIC, μg/ml) of some of the compounds and their efficacy (as indicated by $ED_{50}$) in treating mice infected with microorganisms of the genus Pseudomonas were compared with those of two compounds known to be effective against the microorganisms of the genus Pseudomonas, i.e. 6-[D(−)-α-(4-ethyl-2,3-dioxo-1-piperazinylcarbonylamino)-phenylacetamido]penicillanic acid (commonly referred to as piperacillin) and 6-[D(−)-α-{3-(3,4-dihydroxybenzoyl)-3-methyl-1-ureido}-α-phenylacetamido]penicillanic acid (described in West German Offenlegungsschrift No. 2,921,324 and hereunder referred to as compound Z).

1. MIC measurement (1) Method

Invitro antibacterial activity was measured by the agar plate doubling dilution method described below. A test culture incubated overnight in a heart infusion broth was diluted by 100 to 1000 fold and one spoonful of the culture was inoculated on heart infusion agars (HI agar) containing various concentrations of a specific compound and the inoculates were incubated at 37° C. for 20 hours.

(2) Results

The results of measurement of the MIC of the test compounds are shown in Table I wherein the compounds are identified by the symbols (a, b, ... f) that are keyed to those used in the Examples.

TABLE 1

| Microorganism | Test compound (µg/ml) | | | | | | | pipera-cillin |
|---|---|---|---|---|---|---|---|---|
| | a | b | c | d | e | f | Z | |
| *Bacillus subtilis* POI-219 | 0.2 | 0.78 | 0.1 | 0.4 | 0.4 | 0.4 | 0.1 | 0.2 |
| *Staphylococcus aureus* 209P | 0.78 | 1.56 | 0.4 | 0.78 | 1.56 | 0.78 | 0.4 | ≦0.2 |
| *Escherichia coli* NIHJ | 0.4 | 6.25 | 0.4 | 0.4 | 0.78 | 0.78 | 0.2 | 0.2 |
| *Shigella flexneri* 2b | ≦0.1 | ≦0.1 | ≦0.1 | ≦0.1 | ≦0.1 | ≦0.1 | ≦0.1 | 0.78 |
| *Salmonella paratyphi* A | ≦0.1 | ≦0.1 | ≦0.1 | ≦0.1 | ≦0.1 | ≦0.1 | ≦0.1 | 0.4 |
| *Klebsiella pneumoniae* 15c | 0.4 | 3.12 | 0.4 | 0.2 | 0.4 | 0.4 | ≦0.1 | 3.12 |
| *Proteus mirabilis* 9' | 1.56 | 3.12 | 1.56 | 0.2 | 0.78 | 1.56 | 0.78 | 0.78 |
| *Pseudomonas aeruginosa* J-272 | 0.4 | 0.78 | 0.2 | 0.78 | 0.4 | 0.2 | 0.1 | 12.5 |
| *Pseudomonas aeruginosa* J-169 | 0.78 | 3.12 | 0.78 | 3.12 | 3.12 | 0.78 | 0.2 | 12.5 |
| *Pseudomonas aeruginosa* J-169-CM-222 | 3.12 | 25 | 1.56 | 3.12 | 6.25 | 3.12 | 0.4 | 25 |

2. $ED_{50}$ measurement (1) Method

Five-week-old ddY male mice (five constituting one group) weighing 21 to 25 g on average were administered intraperitoneally with 5% mucin suspensions of test microorganisms that were incubated in brain heart infusion agar plates overnight at 37° C.

One hour and three hours after the inoculation, the mice were injected subcutaneously with various concentrations of the test compounds. The $ED_{50}$ of each test compound was determined from the number of the mice that were still alive five days after injection of the respective doses.

(2) Results

The test results are shown in Table II.

TABLE II

| Test micro-organism | Counts of cells inoculated | $ED_{50}$(SC)mg/head Test compound | | | | | | | pipera-cillin |
|---|---|---|---|---|---|---|---|---|---|
| | | a | b | c | d | e | f | Z | |
| *Pseudomonas aeruginosa* J-272 | 1 × 10⁴ | 0.61 | 1.20 | 1.48 | 1.52 | 1.71 | 1.18 | 2.30 | 10.0 |

The data in Tables I and II shows that the end compounds of this invention have lower in vitro activity than the controls but that they have higher in vivo activity against at least certain strains of the genus Pseudomonas.

The method for producing the end compounds of this invention is now described more specifically by reference to the following examples which are given here for illustrative purposes only and are by no means intended to limit the scope of the invention.

(1) To 70 ml of a suspension of dried dichloromethane containing 5.0 g of N-(3-hydroxypropyl)-3,4-dihydroxybenzamide and 12.9 g of trimethylsilylchloride, 40 ml of a solution of dried dichloromethane containing 11.5 g of triethylamine was added deopwise under cooling with ice water. The resulting mixture was refluxed for 40 minutes in a nitrogen atmosphere. Under cooling, 2.8 ml of trichloromethyl chloroformate was added dropwise at a temperature between −10° and −5° C. The temperature of the mixture was elevated gradually and after stirring at between 0° and 5° C. for 2 hours, excess phosgene and solvent were distilled off under vacuum. Dry dichloromethane (80 ml) was added to the residue and the insoluble portion was filtered off by gravity and subjected to a reaction which is described hereunder.

(2) Trimethylsilyl chloride (7.8 g) was added dropwise at between 5° and 10° C. to 100 ml of a solution of dried dichloromethane containing 10.8 g of anhydrous ampicillin and 7.1 g of triethylamine. After stirring the mixture at the same temperature for one hour, the dichloromethane solution prepared in (1) above was added dropwise at between 0° and 5° C. under stirring. Following stirring at between 5° and 10° C. for one hour, the mixture was evaporated to dryness at room temperature under vacuum, and a mixture of 300 ml of ethyl acetate and 100 ml of cold 1 N-hydrochloric acid was added to the residue and the organic layer was separated. The organic layer was then washed with 300 ml of cold saturated brine, and extracted twice with 300 ml of a cold saturated aqueous solution of sodium hydrogencarbonate. The separated aqueous layer was washed with 100 ml of ethyl acetate. The aqueous layer was mixed with 250 ml of ethyl acetate, treated with cold 6 N-hydrochloric acid to have its pH adjusted to about 1.5, and saturated with sodium chloride. The organic layer was then separated, washed with 100 ml of cold saturated brine, dried with anhydrous magnesium sulfate and the solvent was distilled off under vacuum. The residue was subjected to column chromatography on activated carbon (for chromatograph) and eluted with ethyl acetate. The eluates were combined and concentrated under vacuum until the volume was about 30 ml. The concentrate was added to 300 ml of n-hexane under stirring to give 5.0 g of 6-[D(−)-α-{3-(3,4-dihydroxybenzoyl)-3-(3-hydroxypropyl)-1- ureido}-α-phenylacetamido]penicillanic acid (hereunder referred to as compound (a)) as a white power.

IR $\nu_{max}^{KBr}$ (cm$^{-1}$): 3700–2300, 1775, 1675, 1600, 1515

NMR (DMSO-d$_6$, 60 MHz) δ(ppm): 1.41 (3H, s), 1.55 (3H, s), 1.4–2.0 (2H, br), 3.36 (2H, t, J=6 Hz), 3.75 (2H, br), 4.20 (1H, s), 5.3–5.8 (3H, m), 6.7–7.5 (8H, m), 9.2 (2H, br)

UV $\lambda_{max}^{EtOH}$ nm(ε): 209 (3.1×10$^4$), 295 (6.3×10$^3$) 225 (shoulder), 271 (6.1×10$^3$)

Ferric chloride color reaction: positive (dark green)

(a) By repeating the procedure of Example 1(1) except that 5.0 g of N-(3-hydroxypropyl)-3,4-dihydroxybenzamide was replaced by 5.0 g of N-{2-(2-hydroxyethoxy)ethyl}-3,4-dihydroxybenzamide, 5.2 g of 6-[D(−)-α-[3-(3,4-dihydroxybenzoyl)-3-{2-(2-hydroxyethoxy)ethyl}-1-ureidol]-α-phenylacetamido]-penicillanic acid (hereunder referred to as compound (c)) was obtained as a white powder.

IR $\nu_{max}^{KBr}$ (cm$^{-1}$): 3700–2200, 1775, 1675, 1600, 1515, 1050

NMR (DMSO-d$_6$, 60 MHz) δ(ppm): 1.41 (3H, s), 1.55 (3H, s) 3.3–4.1 (8H, m), 4.20 (1H, s), 5.3–5.8 (3H, m), 6.7–7.6 (8H, m), 9.08 (1H, d, J=7 Hz), 9.20 (1H, d, J=7 Hz)

UV $\epsilon_{max}^{EtOH}$ nm (ε): 207 (2.8×10$^4$), 224 (shoulder), 270 (4.6×10$^3$), 295 (4.6×10$^3$)

Ferric chloride color reaction: positive (dark green)

(b) By repeating the procedure of Example 1(1) except that 5.0 g of N-(3-hydroxypropyl)-3,4-dihydroxybenzamind was replaced by 5.0 g of N-(2-methoxyethyl)-3,4-dihydroxybenzamide, and that trimethylsilyl chloride and triethylamine were used in amounts of 9.7 g and 8.6 g, respectively, 7.0 g of 6-[D(−)-α-{3-(3,4-dihydroxybenzoyl)-3-(2-methyoxyethyl)-1-ureido}-α-phenylacetamide]-penicillanic acid (hereunder referred to as compound (d)) was obtained as a white powder.

IR $\nu_{max}^{KBr}$ (cm$^{-1}$): 3700–2300, 1775, 1675, 1600, 1515, 1055

NMR (DMSO-d$_6$, 60 MHz) δ(ppm): 1.41 (3H, s), 1.56 (3H, s), 3.18 (3H, s), 3.40 (2H, br), 3.85 (2H, br), 4.20 (1H, s), 5.3–5.8 (3H, m), 6.7–7.6 (8H, m), 9.11 (1H, d, J=7 Hz), 9.15 (1H, d, J=7 Hz)

UV $\epsilon_{max}^{EtOH}$ nm (ε): 208 (2.8×10$^4$), 224 (shoulder), 272 (5.9×10$^3$), 295 (5.9×10$^3$)

Ferric chloride color reaction: positive (dark green)

(c) By repeating the procedure of Example 1(1) except that 5.0 g of N-(3-hydroxypropyl)-3,4-dihydroxybenzamide was replaced by 5.0 g of N-(3-acetoxypropyl)-3,4-dihydroxybenzamide and that trimethylsilyl chloride and triethylamine were used in amounts of 8.1 g and 7.2 g, respectively, 3.5 g of 6-[D(−)-α-{3-(3,4-dihydroxybenzoyl)-3-(3-acetoxypropyl)-1-ureido}-α-phenylacetamido]-penicillanic acid (hereunder referred to as compound (e)) was obtained as a white powder.

IR $\nu_{max}^{KBr}$ (cm$^{-1}$): 3700–2300, 1775, 1730, 1680, 1600, 1510

NMR (DMSO-d$_6$, 60 MHz) δ(ppm): 1.41 (3H, s), 1.5–2.1 (2H, br), 1.55 (3H, s), 1.88 (3H, s), 3.6–4.1 (4H, m), 4.21 (1H, s), 5.3–5.8 (3H, m), 6.8–7.6 (8H, m), 9.17 (1H, d, J=7 Hz), 9.30 (1H, d, J=7 Hz)

UV $\epsilon_{max}^{EtOH}$ nm (ε): 205 (2.8×10$^4$), 223 (shoulder), 272 (4.0×10$^3$), 293 (4.4×10$^3$)

Ferric chloride color reaction: positive (dark green)

EXAMPLE 2

(1) To a mixture of 30 ml of dried dichloromethane and 30 ml of tetrahydrofuran that had suspended therein 5.0 g of N-(2-hydroxyethyl)-3,4-dihydroxybenzamide and 13.8 g of trimethylsilyl chloride, 30 ml of a solution of dried dichloromethane containing 12.3 g of triethylamine was added dropwise under cooling with ice water. The resulting mixture was refluxed for 40 minutes in a nitrogen atmosphere. Under cooling, 3.0 ml of trichloromethyl chloroformate was added dropwise at a temperature between −10° and −5° C. The temperature of the mixture was elevated gradually and after stirring at between 0° and 5° C. for 2 hours, excess phosgene and solvent were distilled off under vacuum. Dried dichloromethane (80 ml) was added to the residue and the insoluble portion was filtered off by gravity and subjected to a reaction which is described below.

(2) Trimethylsilyl chloride (8.4 g) was added dropwise at between 5° and 10° C. to 110 ml of a solution of dried dichloromethane containing 11.6 g of anhydrous ampicillin and 7.6 g of triethylamine. After stirring the mixture at the same temperature for one hour, the dichloromethane solution prepared in (1) above was added dropwise at between 0° and 5° C. under stirring. Following stirring at between 5° and 10° C. for one hour, about 100 ml of cold saturated brine was added to the mixture and the organic layer was separated. The organic layer was then washed with 300 ml of cold saturated brine, and extracted twice with 300 ml of a cold saturated aqueous solution of sodium hydrogencarbonate. The separated aqueous layer was washed with 100 ml of ethyl acetate. The aqueous layer was mixed with 250 ml of ethyl acetate, treated with cold 6 N-hydrochloric acid to have its pH adjusted to about 1.5, and saturated with sodium chloride. The organic layer was then separated, washed with 100 ml of cold saturated brine, dried with anhydrous magnesium sulfate and the solvent was distilled off under vacuum. The residue was subjected to column chromatography on Sephadex LH-20 (the trade name for a dextran cross-linked polymer produced by Fine Chemicals Corp.) and eluted with acetone. The eluate was concentrated under vacuum until the volume was about 30 ml. The concentrate was treated with 300 ml of diethyl ether to give 3.0 g of 6-[D(−)-α-{3-(3,4-dihydroxybenzoyl)-3-(2-hydroxyethyl)-1-ureido}-α-phenylacetamide]penicillanic acid (hereunder referred to as compound (b)) as a white powder.

IR $\nu_{max}^{KBr}$ (cm$^{-1}$): 3700–2200, 1770, 1675, 1600, 1510

NMR (DMSO-d$_6$, 60 MHz) δ(ppm): 1.41 (3H, s), 1.56 (3H,s), 3.3–4.1 (4H, m), 4.21 (1H, s), 5.3–5.8 (3H, m), 6.7–7.6 (8H, m), 9.21 (1H, d, J=7 Hz), 9.33 (1H, d, J=7 Hz)

UV $\lambda_{max}^{EtOH}$ nm (ε): 204 (3.3×10$^4$), 221 (shoulder), 266 (5.4×10$^3$), 295 (5.6×10$^3$)

Ferric chloride color reaction: positive (dark green)

EXAMPLE 3

To 70 ml of dried dichloromethane having 12.9 g of amoxicillin trihydrate suspended therein 12.9 g of N,O-bis(trimethylsilyl) acetamide was added at between 10° and 15° C., and stirred to form a homogeneous mixture. To the mixture, a dichloromethane solution as prepared in Example 1(1) was added dropwise at between 5° and 10° C. The mixture was stirred at the same temperature for one hour, and after evaporating the mixture to dryness at room temperature under vacuum, a mixture of 250 ml of ethyl acetate, 50 ml of tetrahydrofuran and 100 ml of cold 1 N-hydrochloric acid was added to the residue, and the organic layer was separated. The organic layer was then washed with 300 ml of cold saturated brine, and extracted twice with 300 ml of a cold saturated aqueous solution of sodium hydrogencarbonate. To the extract, a mixture of 250 ml of ethyl acetate and 50 ml of tetrahydrofuran was added, and its pH was adjusted to about 1.5 with cold 6 N-hydrochloric acid. The aqueous layer was saturated with sodium chloride and the organic layer was separated. The organic layer was washed with 100 ml of cold saturated brine, dried with anhydrous magnesium sulfate, and the solvent was distilled off under vacuum. The residue was subjected to column-chromatography on activated carbon (for chromatography) and eluted with acetone. The eluates were combined and concentrated under vacuum until the volume was about 30 ml. The concentrate was added to 300 ml of ethyl ether under stirring to give 4.5 g of 6-[D(−)-α-{3-(3,4-dihydroxybenzoyl)-3-(3-hydroxypropyl)-1-ureido}-α-(4-hydroxyphenyl-)acetamido]penicillanic acid (hereunder referred to as compound (f)) as a white powder.

IR $\nu_{max}^{KBr}$ (cm$^{-1}$): 3700–2300, 1770, 1680, 1610, 1515

NMR (DMSO-$d_6$, 60 MHz) δ(ppm): 1.42 (3H, s), 1.56 (3H, s), 1.3–1.9 (2H, br), 3.1–4.0 (4H, m), 4.20 (1H, s), 5.3–5.7 (3H, m), 6.5–7.3 (7H, m), 9.0 (2H, br)

UV $\lambda_{max}^{EtOH}$ nm(ε): 206 (2.8×10$^4$), 224 (2.2×10$^4$), 276 (6.6×10$^3$), 283 (6.4×10$^3$), 295 (5.4×10$^3$)

Ferric chloride color reaction: positive (dark green)

EXAMPLE 4

(1) To 100 ml of a suapension of dried dichloromethane containing 4.7 g of D(−)-phenylglycine and 7.8 g of trimethylsilyl chloride, 7.1 g of triethylamine was added at between 5° and 10° C. Then, 1 ml of N,O-bis(trimethylsilyl)acetamide was added dropwise at the same temperature, and following stirring for one hour at room temperature, a dichloromethane solution as prepared in Example 1(1) was added dropwise under stirring at between 5° and 10° C. The mixture was stirred at the same temperature for one hour, and after it was evaporated to dryness at room temperature under vacuum, a mixture of 300 ml of ethyl acetate and 100 ml of cold 1 N-hydrochloric acid was added to the residue, and the organic layer was separated. The organic layer was washed with 300 ml of cold saturated brine and extracted twice with 300 ml of a cold saturated aqueous solution of sodium hydrogencarbonate. To the extract, 250 ml of ethyl acetate was added, and its pH was adjusted to about 1.5 with cold 6 N-hydrochloric acid. The aqueous layer was saturated with sodium chloride and the organic layer was separated. The organic layer was washed with 100 ml of cold saturated brine, dried with anhydrous magnesium sulfate and the solvent was distilled off under vacuum. The residue was crystallized with acetone-chloroform and recrystallized from the same solvent system to give 5.5 g of D(−)-α-{3-(3,4-dihydroxybenzoyl)-3-(3-hydroxypropyl)-1-ureido}-phenylacetic acid as colorless crystals.

m.p. (with decomposition): 139°–141° C.

Elemental analysis: Calculated for $C_{19}H_{20}N_2O_7 \cdot H_2O$: C, 56.16; H, 5.46; N, 6.89 (%) Found: C, 56.30; H, 5.40; N, 6.87 (%)

IR $\nu_{max}^{KBr}$ (cm$^{-1}$): 3540, 3500, 1690, 1670, 1595, 1520

NMR (DMSO-$d_6$, 60 MHz) δ(ppm): 1.3–2.0 (2H, m), 3.35 (2H, t, J=6 Hz), 3.73 (2H, t, J=6.5 Hz), 5.22 (1H, d, J=7 Hz), 6.7–7.5 (8H, m), 9.19 (1H, d, J=7 Hz)

Ferric chloride color reaction: positive (dark green)

(2) To 50 ml of a suspension of dried dichloromethane containing 4.0 g of the phenylacetic acid obtained in (1) above and 4.9 g of trimethylsilyl chloride, 4.2 g of triethylamine was added dropwise at between 5° and 10° C. By stirring the mixture at between 15° and 20° C. for an hour, a solution of trimethylsilylated phenylacetic acid was obtained, and it was subjected to a reaction which is described below.

(3) To 30 ml of a dried dichloromethane solution containing 1.2 g of trichloromethyl chloroformate, 0.8 g of dimethylformamide was added at −20° C., and following stirring at between 0° and 5° C. for one hour, the dichloromethane solution prepared in (2) above was added at −30° C., and the mixture was stirred at between −10° and −15° C. for 1.5 hours. Subsequently, a solution prepared by dissolving 5.5 g of N,O-bistrimethylsilyl acetamide in 50 ml of a dried dichloromethane suspension containing 2.9 g of 6-aminopenicillanic acid was added dropwise to the mixture at between −10° and −15° C. and stirred at the same temperature for one hour.

By performing extraction and purification as in Example 1(2), 4.0 g of compound (a) was obtained. The compound had the same IR, NMR and UV data as that of the compound obtained in Example 1.

(a) By repeating the procedure of Example 4(1) except that N-(3-hydroxypropyl)-3,4-dihydroxybenzamide was replaced by N-(2-hydroxyethyl)-3,4-dihydroxybenzamide, D(−)-α-{3-(3,4-dihydroxybenzoyl)-3-(2-hydroxyethyl)-1-ureido}phenylacetic acid was produced, and the acetic acid was subjected to the same procedure as in Example 4(2) to give compound (b). The compound had the same IR, NMR and UV data as that of the compound obtained in Example 2.

(b) By repeating the procedure of Example 4(1) except that N-(3-hydroxypropyl)-3,4-dihydroxybenzamide was replaced by N-{2-(2-hydroxyethoxy)ethyl}-3,4-dihydroxybenzamide, D(−)-α-[3-(3,4-dihydroxybenzoyl)-3-{2-(2-hydroxyethoxy)ethyl}-1-ureido]-phenylacetic acid as produced, and the acetic acid was subjected to the same procedure as in Example 4(2) to give compound (c). The compound had the same IR, NMR and UV data as that of the compound obtained in Example 1(a).

(c) By repeating the procedure of Example 4(1) except that N-(3-hydroxypropyl)-3,4-dihydroxybenzamide was replaced by N-(2-methoxyethyl)-3,4-dihydroxybenzamide and that the amount of trimethylsilyl chloride and triethylamine was decreased by one molar equivalent, D(−)-α-{3-(3,4-dihydroxybenzoyl)-3-(2-methoxyethyl)-1-ureido}phenylacetic acid was produced, and the acetic acid was subjected to the same procedure as in Example 4(2) to give compound (d). The compound had the same IR, NMR and UV data as that of the compound obtained in Example 1(b).

(d) By repeating the procedure of Example 4(1) except that N-(3-hydroxypropyl)-3,4-dihydroxybenzamide was replaced by N-(3-acetoxypropyl)-3,4-dihydroxybenzamide and that the amount of trimethylsilyl chloride and triethylamine was decreased by one molar equivalent, D(−)-α-{3-(3,4-dihydroxybenzoyl)-3-(3-acetoxypropyl)-1-ureido}phenylacetic acid was produced, and the acetic acid was subjected to the same procedure as in Example 4(2) to give compound (e). The compound had the same IR, NMR and UV data as that of the compound obtained in Example 1(c).

(e) By repeating the procedure of Example 4(1) except that D(−)-phenylglycine was replaced by D(-4-hydroxyphenylglycine, D(−)-α-{3-(3,4-dihydroxybenzoyl)-3-(3-hydroxypropyl)-1-ureido}-α-(4-hydroxyphenyl)acetic acid was produced, and the acetic acid was subjected to the same procedure as in Example 4(2)

to give compound (f). The compound had the same IR, NMR and UV data as that of the compound obtained in Example 3.

EXAMPLE 5

(1) A suspension of 5.0 g of N-(3-hydroxypropyl)-3,4-dihydroxybenzamide in 150 ml of tetrahydrofuran was prepared. To the suspension, 7.64 g of dimethyl dichlorosilane was added, and 11.98 g of triethylamine was added dropwise slowly to the mixture under stirring at room temperature. The mixture was heated for 60 minutes under reflux, cooled to 10° C., mixed with 1.6 ml of trichloromethyl chloroformate, and the mixture was stirred at 25° C. for 3 hours.

(2) A suspension of 9.5 g of anhydrous ampicillin in 100 ml of ethyl acetate was prepared. To the suspension, 6.5 g of trimethylsilyl chloride was added, and 6.1 g of triethylamine was added dropwise slowly to the mixture under stirring while it was cooled with ice. After the mixture was stirred for another one hour at between 5° and 10° C., the tetrahydrofuran solution prepared in (1) above was added to the mixture which was then stirred for one to two hours at about 20° C. After completion of the reaction, 200 ml of water was added to the mixture which was stirred thoroughly. The mixture was left to stand to separate the organic layer. The organic layer was washed with cold saturated brine and extracted with 200 ml of a cold saturated aqueous solution of sodium hydrogencarbonate. The separating aqueous layer was washed with ethyl acetate. Then, 200 ml of ethyl acetate was added to the aqueous layer whose pH was adjusted to about between 1 and 2 with cold 6 N-hydrochloric acid. The aqueous layer was saturated with sodium chloride and the organic layer was separated. The organic layer was washed with 100 ml of cold saturated brine three times, dried with anhydrous magnesium sulfate, and concentrated under vacuum. The concentrate was added to 500 ml of n-hexane under stirring to give 11.5 g of a crude compound (a) as a pale yellow powder. A mixture of 7.0 g of the crude compound (a) and 0.9 g of sodium hydrogencarbonte was dissolved in 30 ml of cold water, and the solution was subjected to column chromatography on DIAION HP-30 (the trade name for an ion exchange resin produced by Mitsubishi Chemical Industries Limited) and eluted first with water, then with hydrous acetone (acetone conc.: 10 v/v%). The eluates were combined, mixed with 200 ml of ethyl acetate and had the pH adjusted to about 1.5 with cold 1 N-hydrochloric acid. The aqueous layer was saturated with sodium chloride and the organic layer was separated. The organic layer was washed with 100 ml of cold saturated brine, dried with anhydrous magnesium sulfate, and concentrated under vacuum until the volume was about 30 ml. The concentrate was added to 300 ml of n-hexane under stirring to provide 5.0 g of compound (a) as a white powder. The compound had the same IR, NMR and UV data as that of the compound obtained in Example 1.

What is claimed is:

1. A compound of the formula

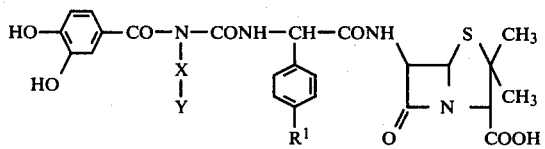

wherein $R^1$ is a hydrogen atom or hydroxyl group; X is a lower alkyl group of $C_{2\text{-}3}$; and Y is bonded to a terminal carbon atom of the substituent of X and means the group $-OR^2$ wherein $R^2$ is a hydrogen atom, a lower alkyl group of $C_{1\text{-}2}$, a lower alkanoyl group of $C_{2\text{-}3}$ or a lower alkyl group of $C_{2\text{-}3}$ substituted with a hydroxyl group; or a pharmaceutically acceptable salt thereof.

2. A compound according to claim 1 wherein $R^2$ is a hydrogen atom, or pharmaceutically acceptable salt thereof.

3. A compound according to claim 1 wherein $-X-Y$ is 3-hydroxypropyl, or a pharmaceutically acceptable salt thereof.

4. A bactericidal composition comprising a pharmaceutically effective amount of a compound according to any one of claims 1, 2 or 3, or a pharmaceutically acceptable salt thereof; and a pharmaceutically acceptable carrier.

* * * * *